US008057642B2

(12) United States Patent
Billig et al.

(10) Patent No.: US 8,057,642 B2
(45) Date of Patent: *Nov. 15, 2011

(54) METHOD OF CORROSION PREVENTION

(75) Inventors: Barry Billig, Irvington, NY (US); James Mann, Brooklyn, NY (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/849,276

(22) Filed: Aug. 3, 2010

(65) Prior Publication Data
US 2010/0314236 A1     Dec. 16, 2010

Related U.S. Application Data

(63) Continuation of application No. 11/405,133, filed on Apr. 17, 2006, now Pat. No. 7,790,001.

(51) Int. Cl.
*B01D 3/34* (2006.01)
*C07C 29/94* (2006.01)
*C23F 11/00* (2006.01)
*C23F 14/00* (2006.01)

(52) U.S. Cl. ............... 202/267.1; 106/14.12; 106/14.21; 159/DIG. 15; 159/DIG. 20; 159/DIG. 21; 203/7; 203/51; 203/86; 252/389.2; 568/913; 34/427

(58) Field of Classification Search ............... 106/14.12, 106/14.21; 252/389.2; 34/427, 523; 159/DIG. 15, 159/DIG. 20, DIG. 21; 202/267.1; 203/7, 203/51, 86; 568/913
See application file for complete search history.

(56) References Cited

U.S. PATENT DOCUMENTS

| 4,623,399 | A |   | 11/1986 | Frenier |
|-----------|---|---|---------|---------|
| 5,294,371 | A |   | 3/1994  | Clubley et al. |
| 5,753,316 | A |   | 5/1998  | Brent et al. |
| 5,788,857 | A | * | 8/1998  | Yang et al. .................... 210/700 |
| 6,066,232 | A | * | 5/2000  | Mohr et al. ................... 159/13.3 |
| 6,133,489 | A |   | 10/2000 | Mohr et al. |
| 6,770,222 | B1 |  | 8/2004  | Ukita et al. |

FOREIGN PATENT DOCUMENTS
JP        2006-36449   *  2/2006
* cited by examiner

*Primary Examiner* — Virginia Monaharan
(74) *Attorney, Agent, or Firm* — Scully, Scott, Murphy & Presser, P.C.

(57) ABSTRACT

This invention relates to a process for reducing the corrosion rate of iron-containing vessels within an ethylene glycol distillation system. The inventive process includes the addition of an additive component of sodium nitrite and sodium hypophosphite into such iron-containing vessels, to thereby react with iron of the inside walls and form a protective coating thereon. This process reduces the corrosion rate in iron-containing vessels of the apparatus, and reduces the catalytic effects of iron corrosion products within the system. Thus, not only is the on-stream time of the vessels extended, but also product quality is improved by reducing the aldehyde content of the final ethylene glycol product.

9 Claims, 4 Drawing Sheets

METHOD OF CORROSION PREVENTION

RELATED APPLICATIONS

This application is a continuation of U.S. Ser. No. 11/405,133, filed Apr. 17, 2006, now U.S Pat. No. 7,790,001 the entire contents of which are incorporated herein by reference.

BACKGROUND OF THE INVENTION

1. Field of the Invention

The present invention relates to corrosion prevention, or more particularly to a method for preventing the corrosion of iron-containing vessels within an ethylene glycol distillation apparatus. This method includes the addition of an additive component to the apparatus, which additive component reacts with iron-containing inside walls of the apparatus vessels. This reaction forms a protective coating on these inside walls, to thereby protect them against corrosion. The additive component also prevents the decomposition of glycols, caused by the presence of iron in an ethylene glycol containing fluid flowing within the apparatus.

2. Description of the Related Art

A variety of ethylene glycol processes are known in the art. Typically, ethylene glycol is produced in a reactor, by the hydrolysis of ethylene oxide in a water stream. The result is an aqueous glycol-containing stream. This process often also result in the formation of light acids, such as acetic acid and formic acid, in the ethylene oxide reactor. It is economically desirable to produce ethylene glycol without the need for first purifying the ethylene oxide to remove all of its impurities. Thus, various distillation apparatuses for distilling ethylene glycol have been developed. For example, the aqueous glycol-containing stream may be fed into a series of multi-effect evaporator vessels to remove water, resulting in a concentrated glycol stream. This concentrated glycol stream may then be distilled by a series of reboilers and separated into monoethylene glycol, diethylene glycol, and triethylene glycol end products.

Additional output streams from an ethylene oxide reactor, which may contain acid salts and glycol, can be treated in an ion exchange unit to remove the acid salts and recover glycol. The treated output stream, although free of acid salts, contain esters of acids. While some of the esters are hydrolyzed and removed in the ion exchange unit, the bulk of them pass through this unit. The treated output stream, along with a distillation recycle stream, is fed into the multi-effect evaporator vessels to remove water from the glycol. The distillation recycle stream also contains glycolic esters of heavier acids such as glycolic acid and oxalic acid. The glycolic esters are hydrolyzed at high temperatures in the evaporator vessels, releasing free acids. Unfortunately these acids corrode the carbon steel of the evaporator vessels. In addition, undesirable iron products, generally in the form of magnetite, are carried with the concentrated glycol stream and coat the inside walls of downstream reboilers. At high reboiler temperatures the catalytic effect of the iron products causes the decomposition of glycol, forming carbon and aldehydes. Resulting carbon deposits on the reboiler walls necessitate frequent cleaning, which shortens the on-stream time of the reboilers. Furthermore, aldehydes generated by the glycol decomposition enter the monoethylene glycol (MEG) product, affecting the product quality. In fact, some plants require repeated cleaning of the reboilers just to maintain the product specification.

It would therefore be desirable to develop a method for preventing corrosion of iron-containing apparatus components, and for preventing glycol decomposition caused by catalytic interaction with iron. The present invention provides a solution to these problems.

It has now been found that the addition of a composition of sodium nitrite and sodium hypophosphite into the distillation apparatus reduces the corrosion rate in iron-containing vessels and reduces the catalytic effects of iron corrosion products in the downstream reboilers. This not only extends the on-stream time of the reboilers, but also improves the product quality by reducing the aldehyde content of the MEG product.

SUMMARY OF THE INVENTION

The invention provides a method for reducing corrosion of an ethylene glycol distillation apparatus, which comprises:

a) providing an ethylene glycol distillation apparatus comprising an evaporator vessel and a drying vessel connected thereto, at least one of said evaporator vessel and said drying vessel having inside walls which comprise iron;

b) flowing an ethylene glycol containing fluid through the evaporator vessel and then through the drying vessel; and c) introducing an additive component comprising sodium nitrite and sodium hypophosphite into the evaporator vessel and/or drying vessel while flowing the ethylene glycol containing fluid through the evaporator vessel and the drying vessel, such that the additive component reacts with iron of the inside walls of the evaporator vessel and/or the drying vessel, thereby forming a protective coating on the inside walls of the evaporator vessel and/or the drying vessel.

The invention also provides a method for distilling ethylene glycol, which comprises:

a) providing an ethylene glycol distillation apparatus comprising an evaporator vessel and a drying vessel connected thereto, at least one of said evaporator vessel and said drying vessel having inside walls which comprise iron;

b) flowing an ethylene glycol containing fluid which comprises water, through the evaporator vessel to thereby remove at least a portion of the water to thereby form a concentrated ethylene glycol stream, which concentrated ethylene glycol stream then flows through the drying vessel to remove additional water;

c) introducing an additive component comprising sodium nitrite and sodium hypophosphite into the evaporator vessel and/or the drying vessel while flowing the ethylene glycol containing fluid through the evaporator and/or the drying vessel, such that the additive component reacts with iron of the inside walls of the evaporator vessel and/or the drying vessel, thereby forming a protective coating on the inside walls of the evaporator vessel and/or the drying vessel; and d) extracting a distilled ethylene glycol product from the ethylene glycol distillation apparatus.

The invention further provides a vessel having inside walls comprising iron, said walls having a protective coating formed thereon, which protective coating comprises a reaction product formed by a reaction between iron of the vessel's inside walls, and an additive composition comprising sodium nitrite and sodium hypophosphite.

The invention still further provides a distillation apparatus which comprises:

a) an evaporator arrangement comprising at least one evaporator vessel having an entry port capable of accepting a fluid into the evaporator vessel, and an exit port capable of releasing a fluid from the evaporator vessel, and b) a distillation arrangement comprising at least one drying vessel having an entry port capable of accepting a fluid into the drying vessel, and an exit port capable of releasing a fluid from the drying vessel;

wherein the exit port of the evaporator vessel is connected to the entry port of the drying vessel;

and wherein at least one of the evaporator vessel and the drying vessel has inside walls comprising iron, which inside walls comprising iron have a protective coating formed thereon, said protective coating comprising a reaction product formed by a reaction between the iron of said inside walls comprising iron and an additive composition comprising sodium nitrite and sodium hypophosphite.

DETAILED DESCRIPTION OF THE INVENTION

The invention relates to a method for reducing the corrosion of iron-containing equipment in a continuous system which includes an ethylene glycol distillation apparatus. The reduction of such corrosion and the tying up of iron flowing through the apparatus has the benefits of reducing the fouling of components of the distillation apparatus, and reducing the formation of aldehydes in the reboilers which affect product quality in the ethylene glycol output.

Figure 1:
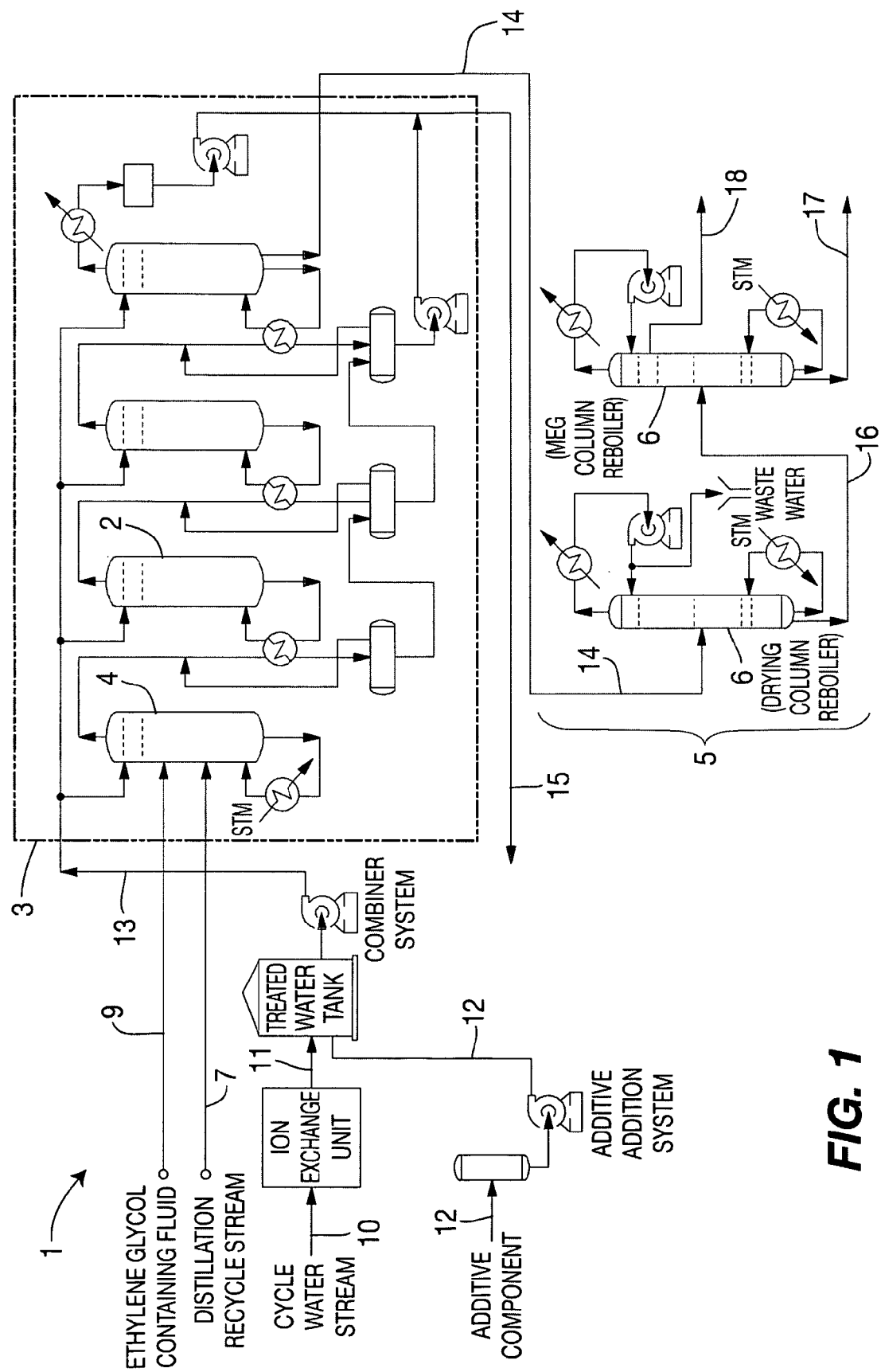
FIG. 1 shows a schematic view of an ethylene glycol distillation apparatus, as well as the locations of component additions according to the inventive method.

FIG. 1 shows an embodiment where an ethylene glycol distillation apparatus 1 includes an evaporator arrangement 3 having at least one multi-effect evaporator vessel 4, and a distillation arrangement 5 connected to the evaporator arrangement 3, which distillation arrangement 5 has at least one drying vessel 6.

According to this invention, at least one of the evaporator vessel 4 and/or the drying vessel 6 has inside walls comprising iron. In specific embodiments, the evaporator vessel inside walls and/or the drying vessel inside walls comprise carbon steel.

The evaporator vessel 4 serves to remove water from fluids which are flowed therethrough. Multi-effect evaporator vessels are well known in the art, and may be purchased commercially. Preferably, the evaporator vessel includes an entry port for accepting fluid into the evaporator vessel, and an exit port for releasing fluid from the evaporator vessel. As shown in FIG. 1, the evaporator arrangement 3 may comprise a series or "train" of multiple connected evaporator vessels. In one specific embodiment, the invention comprises an evaporator arrangement comprising a plurality of interconnected evaporator vessels, including a first evaporator vessel, a last evaporator vessel, and optionally one or more intermediate evaporator vessels connected therebetween. Where multiple evaporator vessels are present, it is preferable that each includes an entry port and exit port as described above, and that the evaporator vessels are sequentially connected from exit port to entry port. In other words, an exit port of a previous evaporator vessel is connected to the entry port of a next evaporator vessel. The evaporator vessels may be connected using any conventional means, including connectors such as piping, tubing, or the like. These connectors may also include a material comprising iron, and they may comprise substantially the same or similar materials as the evaporator vessels. For example, the connectors may comprise carbon steel or the like.

The drying vessel 6, which serves as a distillation vessel, removes additional water from a fluid stream flowing therethrough, resulting in a distilled ethylene glycol product in line 16. Examples of suitable drying vessels include evaporation vessels, reboilers, and the like, which are well known in the art, and may be purchased commercially. Preferably the drying vessel includes an entry port for accepting fluid into the drying vessel, and an exit port for releasing fluid from the drying vessel. As shown in FIG. 1, the distillation arrangement 5 may comprise a series or "train" of multiple connected drying vessels. In one specific embodiment, the invention comprises a distillation arrangement comprising a plurality of interconnected drying vessels, including a first drying vessel, a last drying vessel, and optionally one or more intermediate drying vessels connected therebetween. Where multiple drying vessels are present, it is preferable that each includes an entry port and exit port as described above, and that the drying vessels are sequentially connected from exit port to entry port. In other words, an exit port of a previous drying vessel is connected to the entry port of a next drying vessel. The drying vessels may be connected using any conventional means, including connectors such as piping, tubing, or the like. These connectors may also include a material comprising iron, and may comprise substantially the same or similar materials as the drying vessels. For example, the connectors may comprise carbon steel or the like. FIG. 1 shows one embodiment wherein the invention comprises a distillation arrangement comprising a plurality of sequentially connected drying vessels, including a drying column reboiler and a monoethylene glycol (MEG) column reboiler. In a preferred embodiment, at least one of the drying column reboiler and the monoethylene glycol column reboiler has inside walls which comprise iron. The distillation arrangement may further comprise additional column reboilers, such as at least one diethylene glycol (DEG) column reboiler, and/or at least one triethylene glycol (TEG) column reboiler.

In an embodiment of the present invention, a concentrated ethylene glycol stream 14 flows from an evaporator vessel of the evaporator arrangement 3 through a drying vessel 6 of the distillation arrangement 5 in order to remove additional water from a concentrated ethylene glycol stream 14, resulting distilled ethylene glycol product in line 16, as described below. The distillation arrangement 5 is preferably connected to the evaporator arrangement 3 via a connection between a drying vessel 6 and an evaporator vessel 4 of the apparatus 1. The distillation arrangement 5 may be connected to the evaporator arrangement 3 using any suitable conventional means such as a connector including piping, tubing, or the like. In one preferred embodiment, an exit port of the evaporator vessel 4 is connected to an entry port of the drying vessel 6. In another embodiment, an exit port of the evaporator vessel is connected to an entry port of a drying column reboiler, and an exit port of the drying column reboiler is connected to an entry port of a monoethylene glycol column reboiler.

In certain embodiments, the evaporator vessel 4 and/or the drying vessel 6 may include an internal tray or packing 2. This may be desirable in the inventive process, for example to prevent undesired materials from going overhead in the vessels. For example, such an internal tray or packing would prevent glycol from going overhead in the evaporator vessel 4 and entering other streams, such as a recycle condensate 15 as shown in FIG. 1. Entry of additional glycol into the recycle condensate 15 would be undesirable since bringing additional glycol back to a reactor where glycol is produced would increase the formation of diethylene glycol (DEG) instead of the desired monoethylene glycol (MEG). A combination of such internal trays or packing, along with a reflux flow 13 would keep the glycol from going overhead and entering the recycle condensate 15.

According to the inventive method, an ethylene glycol containing fluid stream 9 is flowed through the ethylene glycol distillation apparatus 1. The ethylene glycol containing fluid stream 9 may be previously purchased or produced using any suitable conventional method. In one embodiment, the ethylene glycol containing fluid stream 9 is produced in a glycol reactor, via the hydrolysis of ethylene oxide in a water stream. Such glycol reactors are known in the art. The ethylene glycol containing fluid stream 9 preferably comprises an aqueous mixed glycol stream. In a particular embodiment, the ethylene glycol containing fluid stream 9 contains about 12% glycol. The fluid stream 9 may also contain acids such as light acids or the like, or other corrosive materials which may have been introduced into the fluid stream 9 via other streams, such as a recycle condensate 15 or the like as shown in FIG. 1.

The ethylene glycol containing fluid stream 9 is flowed through the evaporator vessel 4 to remove water from the fluid stream 9, subsequently forming a concentrated ethylene glycol stream 14. Along with the ethylene glycol containing fluid stream 9, a distillation recycle stream 7 may also be flowed through the evaporator vessel. The distillation recycle stream 7 may contain glycols as well as heavy acids and esters such as glycolic acid and oxalic acid from the distillation arrangement 5 of the apparatus 1, described below. In some cases these materials may exist as a result of air leaks in the drying vessel columns, whereby air oxidizes the glycol into acid forms. Flowing the distillation recycle stream 7 through the evaporator vessel 4 serves to remove water from the glycol, and the recovered glycol becomes part of the concentrated ethylene glycol stream 14.

As illustrated in FIG. 1, a cycle water stream 10 from a glycol reactor or the like may be present and may contain acid salts and glycol. As shown in the embodiment of FIG. 1, the cycle water stream 10 may be treated in an ion exchange unit 8 to remove the acid salts, and to recover glycol. The treated output stream 11, although free of acid salts, contains esters of acids. While some of the esters are hydrolyzed and removed in the ion exchange unit 8, the bulk of them pass through this unit. The ion exchange unit 8 may be connected to the evaporator vessel 4 using any suitable conventional means, including those described herein. The treated output stream 11, is fed into the evaporator vessel 4 to remove water from the glycol, and the recovered glycol becomes part of the concentrated ethylene glycol stream 14.

The concentrated ethylene glycol stream 14 next flows from the evaporator vessel 4 to a drying vessel 6 of the distillation arrangement 5, via a connection such as a pipe or tube as described above. Additional water is removed from the concentrated ethylene glycol stream, such as via a drying column reboiler shown in FIG. 1. A distilled ethylene glycol product 16 may be extracted from a suitable component of the ethylene glycol distillation apparatus. In a preferred embodiment, the distilled ethylene glycol product 16 is extracted from an ethylene glycol column reboiler which is connected to a drying column reboiler of the distillation arrangement. In one embodiment, a distilled monoethylene glycol product in line 18 is isolated using a monoethylene glycol column reboiler, and extracted. Additional reboilers may be used to isolate diethylene glycol and triethylene glycol end products from the remainder stream 17.

An important feature of the invention is the introduction of a non-volatile additive component into the ethylene glycol distillation apparatus 1. The inventive additive component 12 comprises sodium nitrite and sodium hypophosphite. The additive component reacts with iron of the inside walls of the evaporator vessel 4 and/or the drying vessel 6, whichever has inside walls comprising iron, thereby forming a protective coating such as a passive film on those inside walls comprising iron, of the evaporator vessel 4 and/or the drying vessel 6. That is, the protective coating comprises a reaction product formed by a reaction between the iron of said inside walls comprising iron, and the additive composition. The protective coating protects the evaporator vessel and/or the drying vessel, whichever has iron-containing inside walls, as well as other components of the apparatus 1 which may have inside walls comprising iron, from corrosive materials such as acids which may be present in fluids flowing through the vessel or vessels. The additive component 12 preferably reacts with any iron which may be present in the ethylene glycol containing fluid flowing through the vessels. Furthermore, in a preferred embodiment, the additive component 12 reduces an aldehyde content of the ethylene glycol containing fluid.

Where the fluid flows through the apparatus 1 at certain high velocities, the inventive protective coating may fail to form, or it may be washed off of the inside walls of the apparatus vessels. Thus, it is preferred that the fluid is flowed through the apparatus at a velocity which will not hinder the forming of the protective coating, or wash the coating off of the inside walls. Suitable velocities can easily be determined by those skilled in the art.

It is also important that the additive component is non-volatile, that is, the additive component and its components would not degrade or undergo consequential reactions during normal operating procedures or temperatures required for operation of a conventional ethylene glycol distillation apparatus as described herein.

The additive component may be formed in any suitable manner such as mixing or the like. In one embodiment the preferred weight ratio of sodium nitrite to sodium hypophosphite in the additive component 12 ranges from about 4 parts to 1, to about 0.5 parts to 1, with a most preferred weight ratio being about 2 parts to 1. In one embodiment, the additive component 12 comprises an aqueous solution comprising sodium nitrite and sodium hypophosphite. In such an aqueous additive component solution, sodium nitrite and sodium hypophosphite are preferably present together in a total amount of from about 0.5 to about 15 wt % of the aqueous additive component solution, more preferably from about 1 to about 10 wt %, and most preferably from about 1 to about 4 wt % of the aqueous additive component solution.

Figure 2:
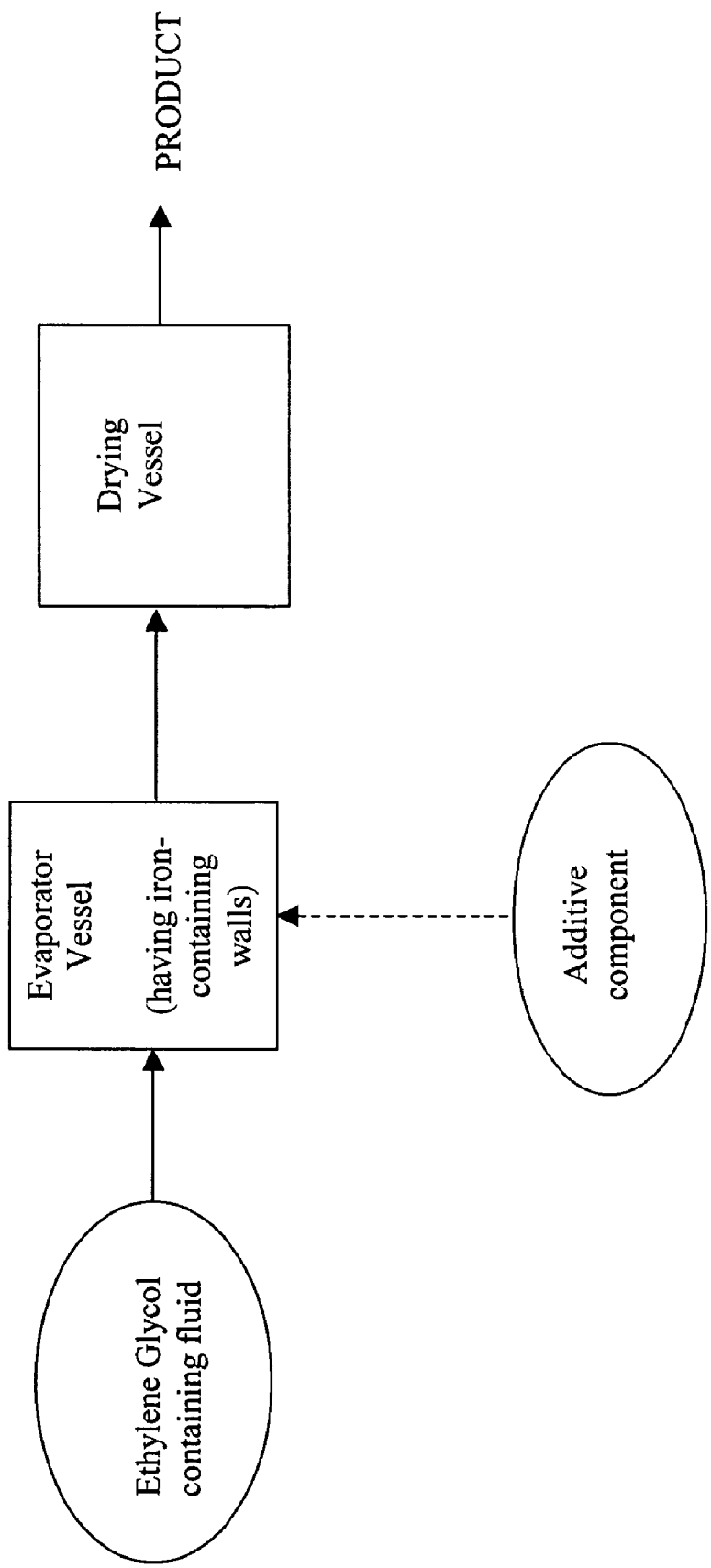
FIG. 2 shows a flow chart illustrating the addition of an additive component to a distillation apparatus wherein the evaporator vessel has inside walls containing iron.
Figure 3:
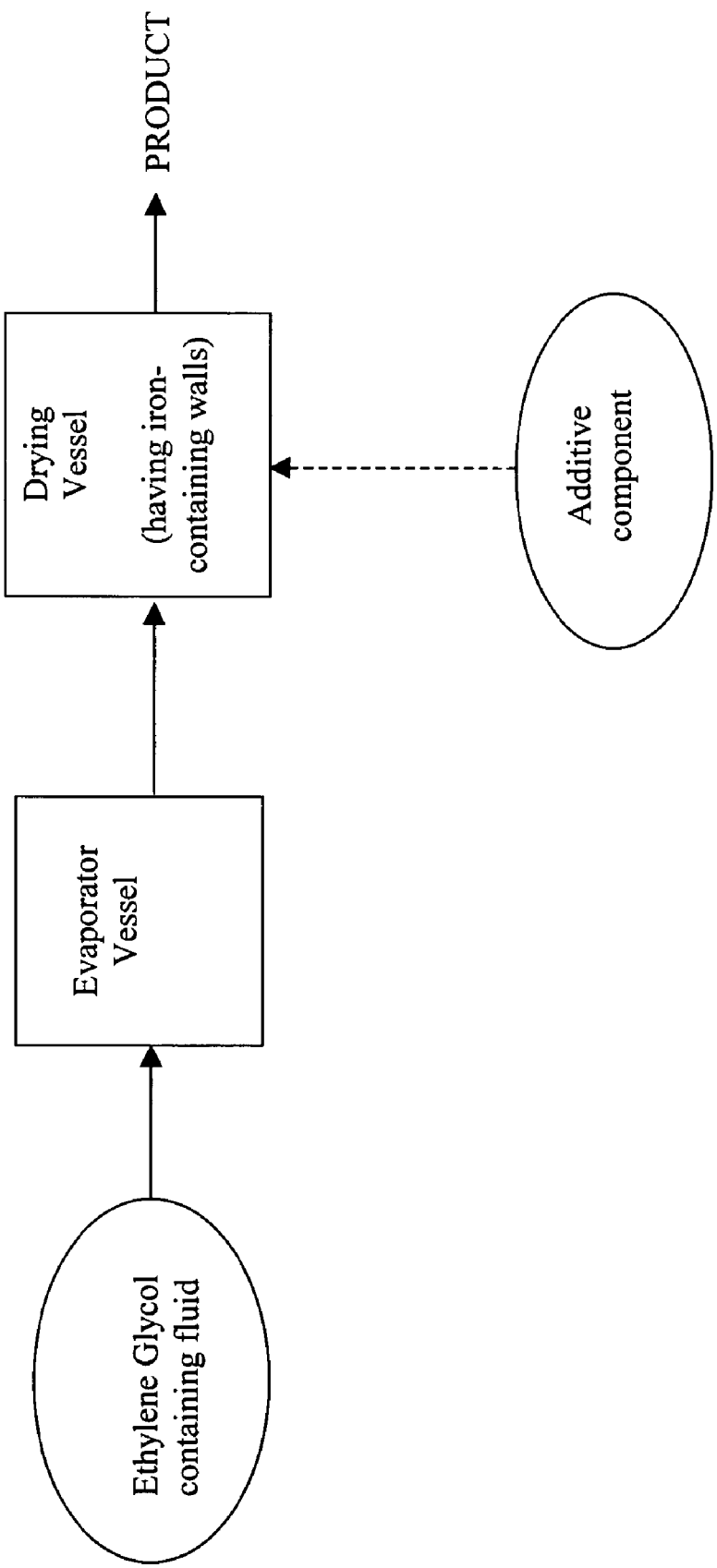
FIG. 3 shows a flow chart illustrating the addition of an additive component to a distillation apparatus wherein the drying vessel has inside walls containing iron.
Figure 4:
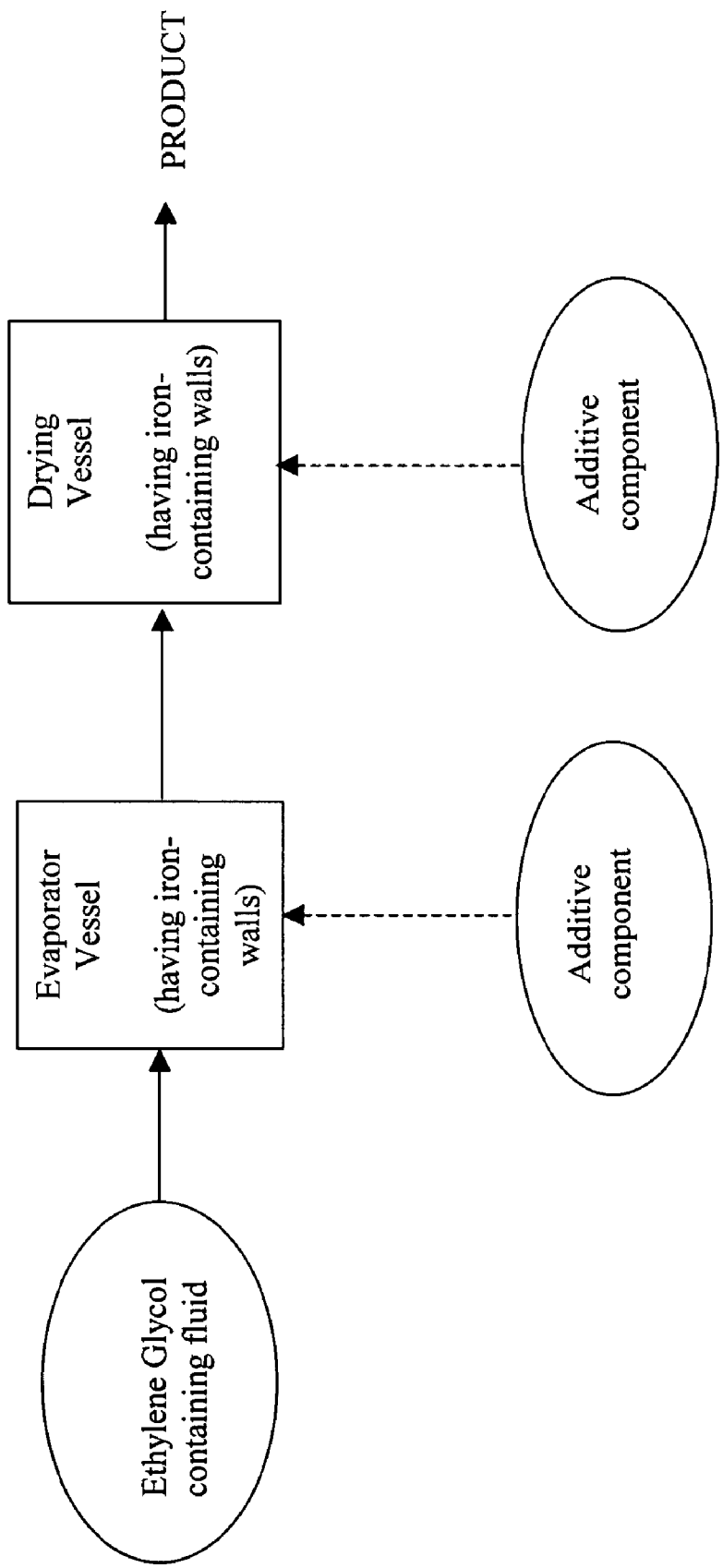
FIG. 4 shows a flow chart illustrating the addition of an additive component to a distillation apparatus wherein both the evaporator vessel and the drying vessel have inside walls containing iron.

The additive component 12 may be introduced into the ethylene glycol distillation apparatus 1 in any suitable manner and at any suitable location. Such may be done, for example, by introduction directly into the evaporator vessel and/or the drying vessel, or by introduction upstream from the evaporator vessel and/or the drying vessel, as shown in FIGS. 2-4. In one embodiment, the additive component 12 is introduced directly into an evaporator vessel 4 comprising iron-containing inside walls. In another embodiment, the additive component 12 is introduced directly into a drying vessel 6 comprising iron-containing inside walls. In certain embodiments, introduction is done by injection. Injection may also be done via a water stream. The apparatus 1 may further comprise, for example, an additive addition system comprising a pump, or an additive addition component such as an injection port or the like. In a preferred embodiment, the additive component 12 is introduced while flowing the ethylene glycol containing fluid 9 through the evaporator vessel 4 and/or the drying vessel 6. As shown in FIG. 1, the additive component 12 may be combined with a treated stream 11 or the like, as described above, to form a combined reflux stream 13 which is then introduced into the evaporator vessel 4.

In certain embodiments, the flow rate of the additive component 12 into the evaporator vessel 4 and/or the drying vessel 6 may be adjusted to maintain a total additive component concentration of sodium nitrite plus sodium hypophosphite ranging from about 3 to about 30 weight ppm in the additive-containing material to be introduced into the evaporator vessel and/or the drying vessel, such as the aqueous additive component solution or the reflux stream 13. A more preferred addition rate would be such that the total additive component concentration ranges from about 5 to about 20, and a most preferred being from about 14 to about 18 wt. ppm in the additive-containing material. In one embodiment, at the preferred addition rate and with a 3 wt. % aqueous additive component solution, 0.53 kg/hr of total additive component per cubic meter per hour would be added to the evaporator vessel and/or the drying vessel. Furthermore, the addition rate may preferably be adjusted to maintain a concentration of from about 2 to about 20 weight ppm of additive component, preferably from about 5 to about 15 weight ppm of additive component, and most preferably from about 8 to about 12 weight ppm of additive component in the concentrated ethylene glycol stream 14 feeding the distillation arrangement 5.

In one specific embodiment which includes the addition of additive component 12 into an evaporator vessel 4, the iron content of the concentrated ethylene glycol stream 14 drops from a typical level of about 2 to about 5 weight ppm for an unprotected apparatus (that is, an apparatus not containing the inventive additive component 12) to an iron content of about 1 ppm by weight or less, for an apparatus which does contain the inventive additive component 12. In one particular embodiment the concentrated ethylene glycol stream 14 has an iron content of from about 0.5 ppm to about 1 ppm by weight of the concentrated ethylene glycol stream. Such a drop in iron content is indicative of a reduced corrosion rate of the evaporator vessel 4. In an embodiment which includes the addition of the additive component 12 into a drying vessel 6, similar indications of corrosion reduction of the drying vessel 6 are shown.

As stated above, the additive component preferably reacts with any iron which may be present in the concentrated glycol stream 14. This reduces the catalytic effects of such iron, namely the decomposition of glycol, which results in the formation of carbon deposits within the drying vessel 6, and the formation of aldehydes which can degrade the quality of the subsequent distilled ethylene glycol product 16. Thus, the additive component preferably reduces the aldehyde content of the distilled ethylene glycol product. In one specific embodiment, the invention's resulting distilled ethylene glycol product 16 shows a drop in aldehyde content from a typical level of about 10 to 12 ppm for an unprotected apparatus (that is, an apparatus not containing the inventive additive component 12) to an aldehyde content of about 4 ppm by weight or less, for an apparatus which does contain the inventive additive component 12. In one particular embodiment, the distilled ethylene glycol product 16 has an aldehyde content of from about 2 to about 4 ppm by weight of the distilled ethylene glycol product. This indicates a reduction of glycol decomposition in the distillation arrangement 5 due to the addition of the inventive additive component 12. The addition of the inventive additive component 12 further results in a lowered fouling rate of drying vessel 6.

Thus the three fold benefit of the inventive additive component includes: reduced corrosion of the vessels; increased service life of the vessels; and improved ethylene glycol product quality. The method of the present invention results in a product quality exhibiting substantial improvement over known procedures which have been developed to deal with each problem individually. For example, while it is known that a caustic injection might help control corrosion in evaporators, previous methods often have a negative impact or no impact on reboiler fouling and ethylene glycol product quality. Therefore the invention herein successfully addresses the above mentioned problems while including additional benefits and counteracting known disadvantages.

This invention further provides a vessel having inside walls comprising iron, which inside walls have a protective coating formed thereon. The protective coating comprises a reaction product formed by a reaction between iron of the vessel's inside walls, and an additive composition comprising sodium nitrite and sodium hypophosphite. In a particular embodiment, the vessel's inside walls comprise carbon steel. The invention still further provides an ethylene glycol distillation apparatus comprising such a vessel, having such a protective coating formed thereon.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. An ethylene glycol vessel having inside walls comprising iron, said walls having a protective coating formed thereon, which protective coating comprises a reaction product formed by a reaction between iron of the vessel's inside walls, and an additive composition comprising sodium nitrite and sodium hypophosphite, the protective coating formed continuously on the inside walls and the protective coating protecting against formation of rust particles.

2. The ethylene glycol vessel of claim 1, wherein the vessel is an evaporator vessel.

3. The ethylene glycol vessel of claim 1, wherein the vessel is a drying vessel.

4. The vessel of claim 1, wherein the additive composition is a composition of sodium nitrite and sodium hypophosphite in a total amount ranging from about 1 to about 4 wt. % in the additive composition.

5. The vessel of claim 4, wherein the additive composition is an aqueous solution.

6. The vessel of claim 1, wherein the weight ratio of sodium nitrite to sodium hypophosphite in the additive composition ranges from about 4:1 to about 0.5:1.

7. The vessel of claim 1, wherein the inside walls comprise carbon steel.

8. The vessel of claim 1, wherein the protective coating is a passive film.

9. The vessel of claim 1, wherein the vessel is a distillation vessel.

* * * * *